United States Patent [19]

Lang et al.

[11] Patent Number: 4,976,952
[45] Date of Patent: Dec. 11, 1990

[54] MACROMOLECULAR, SURFACE-ACTIVE, QUATERNARY, N-SUBSTITUTED CHITOSAN DERIVATIVES AS WELL AS COSMETIC COMPOSITION BASED ON THESE NEW CHITOSAN DERIVATIVES

[75] Inventors: Günther Lang, Reinheim; Harald Wendel, Ober-Ramstadt, both of Fed. Rep. of Germany

[73] Assignee: Wella Aktiengesellschaft, Darmstadt, Fed. Rep. of Germany

[21] Appl. No.: 274,804

[22] PCT Filed: Mar. 10, 1988

[86] PCT No.: PCT/EP88/00183
§ 371 Date: Nov. 14, 1988
§ 102(e) Date: Nov. 14, 1988

[87] PCT Pub. No.: WO88/08698
PCT Pub. Date: Nov. 17, 1988

[30] Foreign Application Priority Data

May 9, 1987 [DE] Fed. Rep. of Germany ....... 3715576

[51] Int. Cl.$^5$ .............................................. A61K 7/00
[52] U.S. Cl. .......................................... 424/47; 424/70; 424/71; 536/20; 8/405; 8/406
[58] Field of Search .................. 424/47, 70, 71, 73; 536/20; 8/405, 406

[56] References Cited

U.S. PATENT DOCUMENTS

| | | | |
|---|---|---|---|
| 4,772,689 | 9/1988 | Lang et al. | 424/47 |
| 4,772,690 | 9/1988 | Lang et al. | 424/47 |
| 4,780,310 | 10/1988 | Lang et al. | 424/47 |
| 4,822,598 | 4/1989 | Lang et al. | 424/47 |
| 4,835,266 | 5/1989 | Lang et al. | 424/71 |
| 4,845,204 | 7/1989 | Lang et al. | 424/47 |

FOREIGN PATENT DOCUMENTS 0192925 8/1984 European Pat. Off. .
0115574 9/1986 European Pat. Off. .

Primary Examiner—Merrell C. Cashion, Jr.
Assistant Examiner—P. L. Prater
Attorney, Agent, or Firm—Michael J. Striker

[57] ABSTRACT

The cosmetic agent for the treatment of the hair and skin contains macromolecular surface-active, quaternary N-substituted chitosan derivatives having the formula (I)

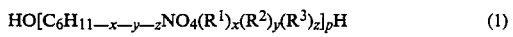

$$HO[C_6H_{11-x-y-z}NO_4(R^1)_x(R^2)_y(R^3)_z]_pH \qquad (1)$$

wherein x is from 0.04–0.4; y is from 0.04–0.92; z is from 0.04–0.92; $(x+y+z) \leq 2$; p is an integer from 100–100,000; $R^1$ is acetyl;

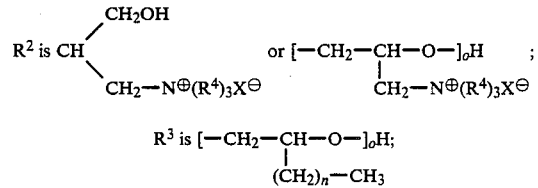

$R^4$ is a $C_1$ to $C_4$-alkyl radical; X is Cl, Br, I or $CH_3SO_4$; o is 1–5; n is 5–20. The present invention also comprises chitosan derivatives having the formula (I). The chitosan derivatives are distinguished particularly by their surface-active properties, for example, their foam-forming and emulsifying properties, and by their hair-setting and hair-conditioning effect.

17 Claims, No Drawings

MACROMOLECULAR, SURFACE-ACTIVE, QUATERNARY, N-SUBSTITUTED CHITOSAN DERIVATIVES AS WELL AS COSMETIC COMPOSITION BASED ON THESE NEW CHITOSAN DERIVATIVES

Our present invention relates to a cosmetic agent for the treatment of the hair and skin. This composition contains macromolecular surface-active, quaternary N-substituted compounds which are derived from chitosan and are used in a suitable cosmetic base.

Our present invention also relates to macromolecular, surface-active, quaternary N-substituted chitosan derivatives.

The use of cationic polymers, preferably polymers containing quaternary ammonium groups, as conditioning agents, in cosmetics, particularly for the treatment of hair, is known. Because of an interaction between their ammonium groups and the anionic groups of the hair the cationic polymers have a great affinity for the keratin fiber.

It has been found that the use of this type of cationic polymer in these cosmetic agents has many advantages; the disentanglement of the hairs and their treatment are made more easy. Furthermore, sheen and bounce are imparted to the hair. However, because of their affinity for keratin these polymers tend to accumulate on the hair so that it becomes heavier and this is undesirable for the final effect.

Furthermore, the synthetic polymers cause problems due to the physiological effect of possibly present monomer traces, which are difficult to remove from the polymer.

Attempts were made to overcome the above-mentioned disadvantages by applying, in these cosmetic compositions, water-soluble salts of chitosan, i.e., a polyglucosamine producible by deacetylation of chitin. In this connection the applicant's European Patent No. 0 002 506 and German Patent No. 26 27 419 are referred to.

In the same manner as in the majority of the cation-active polymers with quaternary groupings chitosan frequently has the disadvantage that it is only slightly compatible with the anionic surface-active compounds conventionally used in hair treatment agents, particularly in shampoos. Therefore, it is necessary to cause the chitosan to react in separate treatments, namely prior to and/or after shampooing. Furthermore, it has been found that chitosan is practically insoluble in a neutral and alkaline medium so that, for example, its application is not possible in alkaline permanent wave agents or hair dyes.

Most of the above-mentioned disadvantages can be avoided by the application of specific water-soluble cation-active chitosan derivatives according to the applicant's DE-OS No. 32 45 784, DE-OS No. 35 01 891 and DE-OS No. 35 02 833 instead of chitosan salts. However, when using these chitosan derivatives in aerosol foam preparations or emulsions it is still required to add to said these surface-active compounds, as for example, cationic surfactants, as emulsifiers or foam-forming agents since these emulsifier or foam-forming agents have no emulsifying or foam-forming properties. However, the physiological compatibility of the agents is impaired by the addition of emulsifiers so that irritations of the skin, of the scalp or of the eyes can result.

It is an object of our invention to provide a cosmetic composition or agent based on cation-active chitosan derivatives which requires a reduced number of additives such as surface-active compounds or emulsifiers.

It is another object of our invention to provide an improved surface-active cationic chitosan derivatives.

SUMMARY OF THE INVENTION

Therefore, the present invention provides water-soluble chitosan derivatives having setting and conditioning properties as well as emulsifying and foam-forming properties while the physiological compatibility is good.

On continuing the tests with chitosan and the compounds derived therefrom, it has been found that specific water-soluble cationic chitosan derivatives have the properties of both a polymer and a surfactant.

The application of these chitosan derivatives allows, for example, the production of foam fixatives having outstanding foaming and setting properties without the use of additional foam-forming agents or polymers. Furthermore, when using these surface-active chitosan derivatives in emulsions they are able to act simultaneously as emulsifiers and as conditioners.

Unlike the cosmetic agents used heretofore, i.e., those based on cationic surfactants or emulsifiers, the physiological compatibility of the agent based on the cationic chitosan derivatives is very good since the penetration depth of the chitosan derivative in the skin is only very slight due to the size of their molecules.

With these cationic surface-active chitosan derivatives a cosmetic agent for the treatment of the hair and skin can thus be produced, i.e., an or composition which is distinguished by surprisingly favorable properties and contains, in a suitable cosmetic base, a macromolecular, surface-active, quaternary N-substituted compound that is derived from chitosan and has the general formula (I)

$$HO[C_6H_{11-x-y-z}NO_4(R^1)_x(R^2)_y(R^3)_z]_pH \qquad (I),$$

wherein x can assume any numerical value from 0.04 to 0.4; y can assume any numerical value from 0.04 to 0.92 and z can assume any numerical value from 0.04 to 0.92 on the condition that $(x+y+z) \leq 2$, p represents an integer from 100 to 100,000, $R^1$ represents the radical

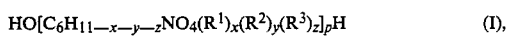

$R_2$ represents the radical

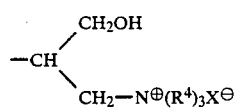

or

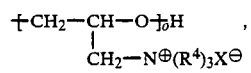

wherein $R^4$ represents $C_1$ to $C_4$-alkyl group, x represents Cl, Br, I or $CH_3SO_4$ and o represents an integer from 1 to 5 and $R^3$ represents the radical

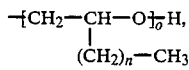

wherein n represents an integer from 5 to 20 and o represents an integer from 1 to 5.

The agent according to the present invention containing a quaternary chitosan derivative having the formula (I) is quite generally suitable for the treatment of the skin and hair. It can be in the form of an aerosol foam, dressing lotion, hair-drying solution, agent for setting the hairdo, washing lotion hair curling agent, anti-dandruff agent, agent for permanent hair shaping, agent for dyeing and decolorizing hair, agent for application prior to or after dyeing the hair and in the form of a cosmetic agent for the care, protection and cleaning of the skin. Examples of this type of agent for the care and cleaning of the skin are face lotions, shaving lotions, moisturizing creams, cold creams, body lotions, sun screen agents or even make-up preparations.

The content of the novel chitosan derivative having the formula (I) in the cosmetic agent according to the present invention is suitably 0.05 to 10 percent by weight, preferably 0.05 to 3 percent by weight.

For the production of a cosmetic base the cosmetic agent according to our present invention can contain, in addition to the chitosan derivative having the formula (I), all the ingredients conventionally used in agents for the treatment of the hair and skin, particularly anionic, cationic, amphoteric, zwitter-ionic or non-ionic surface-active compounds (surfactants), foam synergists, stabilizers, sequestering agents, pigments, thickeners, emulsifiers, buffer substances, preservatives, dyes, perfume oils, conventional cosmetic polymers, such as anionic, non-ionic, cationic or amphoteric polymers, natural substances, cosmetic oils, fatty alcohols, waxes, foam stabilizers, active ingredients against dandruff, reducing agents and propellants.

The cosmetic composition according to our present invention preferably has a pH value of 2 to 11 and can be in the form of an aqueous or aqueous-alcoholic preparation, for example, with an alcohol containing 1 to 4 carbon atoms, as a solution, as a cream, as a gel, as a dispersion or as an emulsion. It is also possible to spray this agent with the aid of an atomizer or other suitable sprayer or to remove it in mixture with conventional propellants, that liquefy under pressure, as aerosol spray or aerosol foam from a pressure vessel.

When the composition according to our present invention is an agent for fixing the hairdo, for example, a hair setting lotion or hair spray, then it usually is in the form of an aqueous or aqueous-alcoholic solution, which is characterized by a content of a quaternary compound having above-defined formula (I). In this case the quaternary chitosan derivative having the formula (I) can be used by itself as a film-forming or setting resin. However, the hair setting agent according to the present invention can also additionally contain other film-forming natural or synthetic polymers. For example, shellac, alginates, gelatin, pectins and cellulose derivatives are suitable as natural polymers. Suitable synthetic polymers are, for example, polyvinyl pyrrolidone, polyvinyl acetate, polyacryl compounds such as acrylic or methacrylic acid polymers, basic polymers of esters of acrylic acid or methacrylic acid with amino alcohols and the salts or quaternization products of these basic polymers, polyacrylonitrile as well as co- or ter-polymers from these compounds, for example, polyvinyl pyrrolidone-vinyl acetate.

This agent then has particularly a pH value of between 4 and 8. This type of agent for setting the hairdo usually contains the film-forming polymers in a total amount of approximately 0.05 to 3.0 percent by weight. When the agent also contains other film-forming polymers in addition to the quaternary chitosan derivative having the formula (I), then the content of quaternary chitosan derivative having the formula (I) decreases correspondingly.

Particularly the lower alcohols conventionally used for cosmetic purposes and containing 1 to 4 carbon atoms, as for example, ethanol and isopropanol, are suitable alcohols.

When the agent for fixing the hairdo is in the form of a foam preparation, which is dispensed from a pressure vessel, then it contains approximately 10 to 60 percent by weight of a propellant.

The following compounds can be used as propellants:—chloro-fluoro alkanes, as for example $CCl_3F$, $CCl_2F_2$, $C_2Cl_3F_3$, $(CCl_2F)_2$, $CHCl_2F$ and $(CClF_2)_2$, readily volatile hydrocarbons, as for example, n-butane and n-propane or even dimethyl ether, carbon dioxide, dinitrogen monoxide, nitrogen, methylene chloride and 1,1,1-trichloroethane. In this agent the quaternary surface-active chitosan derivative having the formula (I) serves simultaneously as a foam-forming agent and as setting component. However, other film-forming natural or synthetic polymers can also be additionally contained in the aerosol foam according to the present invention.

The cosmetic composition according to our invention can also contain the conventional additives for this kind of agent, as for example perfume oil, bactericides or fungicides, combability-improving substances and modifiers, as for example, silicone oil, or softening agents, as for example, isopropyl myristate, phthalic acid diethyl ester and diethyl stearate.

When required, the present agent can simultaneously dye and tint the hair by means of a content of cosmetic dyes. These preparations also are commercially known as dye fixing agents or tint fixing agents, etc. They additionally contain the usual dyes known for hair setting agents, as for example, aromatic nitro dyes (for example, 1,4-diamino-2-nitro-benzene), azo dyes (for example, C.I. 14805-Acid Brown 4), anthraquinone dyes (for example, C.I. 61 015-Disperse Violet 4) and triphenyl-methane dyes (for example, C.I. 42535-Basic Violet 1). Depending on the type of their substituents the dyes of these classes can have an acid, non-ionic or basic character. Their total concentration in these preparations normally is approximately 0.01 to 2.0 percent by weight.

As compared with conventional hair setting cosmetic composition the agent for setting the hairdo in accordance with the present invention has an improved substantivity for the hair, a good combability and a good feel when the hair is wet as well as a particularly pleasant feel when it is in the dried state while setting of the hair is equally good.

Furthermore, the agent described here can also be a shampoo. In that case it is in the form of an aqueous solution or emulsion and contains an anionic, cationic, non-ionic or amphoteric surfactant in addition to the chitosan derivative.

In this shampoo the concentration of the surfactant, relative to the total weight of the agent, usually is between 3 and 50 percent by weight, preferably between 3 and 25 percent by weight, while the pH value usually is between 3 and 9, preferably between 4 and 7. The shampoo according to our invention, usually contains several additives, particularly perfume oil, preservatives, thickeners, foam stabilizers, buffer substances, cosmetic resins, pigments and dyes.

Among the foam stabilizers there are mentioned the fatty amides and particularly the mono- or di-ethanol amides of copra-fatty acids, lauryl or oleic acid mono- or diethanol amide, which are suitably used in amounts of 1 to 10 percent by weight, preferably 1 to 3 percent by weight, relative to the total weight of the agent.

The thickeners suitable for this purpose are the acrylic polymers and the cellulose derivatives, as for example, carboxy methyl cellulose, hydroxy-propyl methyl cellulose and hydroxy-ethyl cellulose. The thickeners usually are present in an amount of 0.1 to 5 percent by weight.

Among the suitable surfactants or surface-active agents which are usual in combination with the quaternary chitosan derivatives the following surfactants are mentioned here:

(a) the anionic surface-active agents, as for example, the alkali metal or alkaline earth, ammonium or alkanol amine salts of alkane sulphonates, alkyl sulphates and alkyl ether sulphates, the $C_{12}$ to $C_{14}$-alkyl sulphate sodium salts or $C_{12}$–$C_{14}$-alkyl triethanol amine salts, the sodium or triethanol amine salts of lauryl or tetradecyl ether sulphates, the disodium salt of sulphosuccinic semiester of alkanol amides, the soaps and the polyether carboxylic acids;

(b) the non-ionic, surface-active agents, as for example, oxyethylated fatty alcohols containing 12 to 18 carbon atoms, for example, lauryl, tetradecyl, cetyl, oleyl, palmityl and stearyl alcohol ethylated with up to 40 moles of ethylene oxide per mole of fatty alcohol, alone or in mixture, the fatty alcohols of oxyethylated lanolin, or oxyethylated lanolin; polyglycerol ether of saturated or unsaturated fatty alcohols and alkyl phenols containing 8 to 30 carbon atoms, in the alkyl radical and 1 to 10 glycerol units in the molecule, as well as fatty acid alkanol amides;

(c) the cationic, surface-active agents, as for example, the dilauryl dimethyl ammonium chloride, the chlorides or bromides of alkyl dimethyl benzyl ammonium, for example, cetyl trimethyl ammonium chloride or bromide, tetradecyl trimethyl ammonium chloride or bromide, the alkyl dimethyl hydroxyethyl ammonium chlorides or bromides, alkyl pyridinium salts, for example, cetyl pyridinium chlorides, the alkyl amide ethyl trimethyl ammonium ether sulphates, imidazoline derivatives, compounds having a cationic character such as amine oxides, for example, alkyl dimethyl amine oxides or alkyl amino-ethyl dimethyl amine oxides;

(d) the amphoteric or zwitter-ionic, surface-active agents, as for example, the carboxyl derivatives of imidazole, the N-alkyl betaines, the N-alkyl sulphobetaines, the N-alkyl-amino-betaines, the N-alkyl-aminopropionates, the alkyl dimethyl ammonium acetates as well as the $C_{12}$ to $C_{18}$-alkyl-dimethylcarboxy-methyl ammonium salts.

The cosmetic composition according to our invention can also be a cream or lotion for use as a hair curative or as a hair care agent. In most cases it is in the form of an oil-in-water or water-in-oil emulsion or suspension and, additionally to the chitosan derivative having the formula (I), it can contain cationic, non-ionic, amphoteric or anionic emulsifiers, and as component of the oil phase it can contain, for example, fatty alcohols, fatty ester or amides and also perfume oils, petrolatum, wool fat alcohol or solid or liquid paraffins.

In case that the above-described agent is an emulsion the quaternary surface-active chitosan derivative is preferably applied as emulsifier and because of its cationic component it simultaneously serves for conditioning the hair. However, conventional surfactants used as emulsifiers can be additionally applied as co-emulsifiers.

When the agent according to our invention is a hair tinting agent or a hair dye, then it is preferably in the form of a cream or lotion and additionally contains conventional hair dyes from the group of the aromatic nitro dyes, azo dyes, anthraquinone dyes, triphenylmethane dyes or even oxidation dyes, for example, from the group of the aromatic diamides and aminophenols. Furthermore, when required, this agent can contain alkalizing agents, antioxidants as well as further cosmetic additives and auxilliary products conventionally used for these agents.

The present agent can also be a permanent shaping agent or fixing agent for the hair. In that case it contains, additionally to the above-mentioned chitosan derivatives having the formula (I), a reducing agent, as for example, thioglycolic acid, thiolactic acid and ammonium sulphite, or an oxidizing agent, as for example, hydrogen peroxide or sodium bromate as well as, when required, alkalizing agents and peroxide stabilizers, for example, phosphoric acid, and other cosmetic auxilliary products and additives, as for example, perfume oils, perfumes, care agents and dyes.

As mentioned hereinbefore, the cosmetic composition according to our invention can also be used for the treatment of skin.

In fact, this cosmetic agent facilitates the moistening of the skin and prevents it from drying out. Furthermore, this agent imparts an excellent soft feel to the skin.

For this purpose the agent according to our invention is preferably in the form of a foam but also can be in the form of a cream, a gel, an emulsion or an aqueous or aqueous-alcoholic solution and the chitosan derivative having the formula (I) is contained therein in a concentration of 0.1 to 10 percent by weight, preferably 0.2 to 6 percent by weight.

The auxiliary products usually contained in this type of cosmetic preparation are, for example, perfumes, dyes, preservatives, thickeners, sequestering agents, emulsifiers, sunscreen agents and the like.

This preparation for the care of the skin is particularly in the form of a foam preparation, a cream or lotion for the care of the hands or of the face or in the form of a sunscreen cream, a coloured cream or of a cleansing cream, a foam bath preparation or a shower bath preparation or even in the form of a deodorant preparation.

This preparation is produced by means of conventional methods. For example, in order to form a cream, an aqueous phase, which contains the chitosan derivative according to our present invention having the formula (I) and, when required, other ingredients or auxiliary products in the dissolved form, and an oil phase are emulsified. For the oily phase various compounds can be used, for example, paraffin oil, vaseline oil, sweet almond oil, avocado oil, olive oil, fatty esters, as for example, glyceryl monostearate, ethyl palmitate and isopropyl palmitate or alkyl myristates, as for example, propyl myristate, butyl myristate, or fatty alcohols and waxes, for example, wool wax and beeswax.

In this cosmetic preparation for the care of the skin the chitosan derivative having the formula (I) can be contained as an auxiliary product or as the principal active ingredient.

The quaternary, surface-active chitosan derivatives having the formual (I), which are contained in the cosmetic agent according to the present invention, are derived from chitosan, i.e., a material obtained by deacetylation of chitin, a naturally occurring acetyl glucosamine.

Chitosan is insoluble in neutral media and in alcaline media. However, because of its chemical nature it forms, in an acid medium, salts that are soluble in specific organic and inorganic acids. Because of its chemical structure and its properties, chitosan is suitable for application in pharmaceutics and cosmetics, in agriculture or as an ion exchanger. However, the commercial utilization, not least because of its insolubility in an aqueous medium, has remained limited to the application as a flocculating agent in the treatment of sewage.

In order to extend the applicability of chitosan, several water-soluble cation-active chitosan derivatives were produced (see the applicant's German Patent Application DE-OS Nos. 32 45 784, DE-OS 35 01 891 and DE-OS 35 02 833). These cation-active chitosan derivatives are supposed to be applicable particularly for setting and conditioning the hair.

It has now been found that by simultaneous reaction of chitosan with a glycide trialkyl ammonium halide (oxirane methane ammonium-N,N,N-trialkyl halide) having the formula (II)

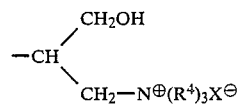

where $R^4$ is $C_1$ to $C_4$-alkyl and x is Cl, Br, I or $CH_3SO_4$ and an epoxide having a long alkyl chain, surface-active cationic chitosan derivatives can be produced. The chitosan derivative, which are soluble in water and in mixtures of water and alcohol, have polymer properties and surfactant properties and thus are suitable for use in a plurality of cosmetic agents, particularly in emulsions and foam preparations.

Therefore, the present invention also relates to macromolecular, surface-active quaternary N-substituted compounds that are derived from chitosan and have the general formula (I)

$$HO[C_6H_{11-x-y-z}NO_4(R^1)_x(R^2)_y(R^3)_z]_pH \quad (I),$$

wherein x can assume any numerical value from 0.04 to 0.4, y can assume any numerical value from 0.04 to 0.92 and z can assume any numerical value from 0.04 to 0.92 on the condition that $(x+y+z) \leqq 2$, p represents an integer from 100 to 100,000, $R^1$ represents the radical

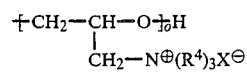

$R^2$ represents the radical

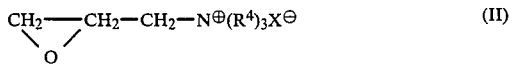

or

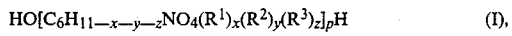

wherein $R^4$ represents $C_1$ to $C_4$-alkyl group, X represents Cl, Br, I or $CH_3SO_4$ and o represents an integer from 1 to 5, and $R^3$ represents the radical

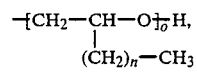

wherein n represents an integer from 5 to 20 and o represents an integer from 1 to 5.

Analogously to the single-stage process described in the applicant's DE-OS No. 32 45 784 the chitosan derivatives are obtained in that chitosan (60 to 96 percent of deacetylacted chitin) is reacted in a suitable solvent or solvent mixture at temperatures of between 20° and 120° C., preferably 80° to 100° C., under pressure in an autoclave, in a suitable ratio with a long-chain epoxide and a glycidyl trialkyl ammonium halide over a period of 5 to 100 hours, preferably 6 to 24 hours.

Suitable long-chain epoxides are particularly alpha-epoxides containing eight(octene-1-oxide) to sixteen (hexadecene-1-oxide) carbon atoms. Suitable glycidyl trialkyl ammonium halides are those containing $C_1$ to $C_4$-alkyl groups, as for example, glycidyl trimethyl ammonium chloride and glycidyl triethyl ammonium chloride.

According to a particularly favorable embodiment of this production process there is used as starting material a chitosan modified by reprecipitating and deep freezing. By using this chitosan the reaction proceeds in a particular favorable manner and with a particularly high yield.

The reaction is preferably carried out in a mixture of water and alcohol, for example, a mixture of water and ethanol.

On completing the reaction possibly present insoluble components are separated from the solutions of chitosan by filtering or centrifuging, when required, followed by neutralizing, whereupon the reaction mixture is concentrated in vacuo. The chitosan derivatives are precipitated immediately or after the dialysis in acetone, alcohols or other suitable solvents.

The present invention will be explained in greater detail by the following Examples.

EXAMPLES

EXAMPLE 1

Reaction of chitosan with octene-1-oxide and glycidyl trimethyl ammonium chloride.

50 g (0.31 mole) of low-molecular chitosan having a Staudinger index (eta) of 140 ml per gram and a degree of deacetylation of 86 percent were dissolved in the equivalent amount of hydrochloric acid and subsequently precipitated by adjusting the pH with a solution of caustic soda to a value of 8. The precipitated, suction-filtered aqueous chitosan was weighed and mixed with ethanol in an amount corresponding to the water content of the ethanol.

The suspension of chitosan in ethanol/water (1:1), together with 159 g (1.24 moles) of octene-1-oxide and 79 g (0.34 mole) of a 65 percent aqueous solution of glycidyl trimethyl ammonium chloride, was stirred for 6 hours at 100° C. The dark brown, almost clear reaction mixture was then filtered whereupon it was concentrated in a rotation evaporator to approximately one half.

By adding the reaction mixture dropwise to 5 to 8 liters of acetone the chitosan was precipitated, whereupon it was filtered with suction and then dried in vacuo.

The yield was 72.3 g.

| Characteristic Data: | |
| --- | --- |
| Staudinger index (eta): | 74 ml/g |
| titratable nitrogen: | 3.76 mmoles/g |
| titratable quaternary nitrogen: | 1.60 mmoles/g |
| degree of substitution cationic: | 0.42 |
| degree of substitution octyl: | 0.31 |

EXAMPLE 2

Reaction of chitosan with hexadecene-1-oxide and glycidyl trimethyl ammonium chloride.

50 g (0.31 mole) of low-molecular chitosan having the same characteristic data as that in Example 1 were reprecipitated in the manner described in Example 1 and mixed with a corresponding amount of ethanol.

The mixture thus obtained was then reacted with 288 g (1.24 moles) of hexadecene-1-oxide and 79 g (0.34 mole) of a 65 percent aqueous solution of glycidyl trimethyl ammonium chloride in an autoclave at 100° C. for 24 hours.

The reaction mixture was then filtered, whereupon the filtrate was concentrated and the chitosan was precipitated with acetone. The reaction product obtained was filtered with suction, dried in vacuo at 50° C. and subsequently ground.

The yield was 84.3 g.

| Characteristic Data: | |
| --- | --- |
| Staudinger index (eta): | 65 ml/g |
| titratable nitrogen: | 3.66 mmoles/g |
| titratable quaternary nitrogen: | 1.95 mmoles/g |
| degree of substitution cationic | 0.53 |
| degree of substitution hexadecy: | 0.13 |

EXAMPLE 3

Reaction of chitosan with tetradecene-1-oxide and glycidyl trimethyl ammonium chloride 50 g (0.31 mole) of chitosan having the same characteristic data as those in Example 1 were pretreated in the manner described in Example 1 and subsequently stirred together with 263 g (1.24 moles) of tetradecene-1-oxide and 79 g (0.34 mole) of a 65% aqueous solution of glycidyl trimethyl ammonium chloride in an autoclave at 100° C. for 6 hours.

On completion of the reaction the chitosan derivative was isolated by precipitation in acetone and then purified and dried in the manner described in Example 1 and 2.

The yield was 72.1 g

| Characteristic Data: | |
| --- | --- |
| Staudinger index (eta): | 97 ml/g |
| titratable nitrogen: | 4.10 mmoles/g |
| titratable quaternary nitrogen: | 2.11 mmoles/g |
| degree of substitution cationic: | 0.51 |
| degree of substitution tetradecyl: | 0.02 |

EXAMPLE 4

Reaction of high-molecular chitosan with octene-1-oxide and glycidyl trimethyl ammonium chloride 25 g (0.155 mole) of a high-molecular chitosan having a Staudinger index (eta) of 1600 ml/g and a degree of deacetylation of 76 percent were reprecipitated analogously to Example 1 and mixed with ethanol in an amount corresponding to that of water contained therein.

The mixture of chitosan, water and ethanol thus obtained was then reacted with 79.5 g (0.62 mole) of octene-1-oxide and 53.5 g (0.23 mole) of a 65 percent aqueous solution of glycidyl trialkyl ammonium chloride for 6 hours in an autoclave at 100° C.

On completion of the reaction the reaction product was precipitated in acetone, filtered with suction, washed twice with acetone and then dried in vacuo at 50° C.

The yield was 37.5 g

| Characteristic Data: | |
| --- | --- |
| Staudinger index (eta): | 406 ml/g |
| titratable nitrogen: | 3.36 mmoles/g |
| titratable quaternary nitrogen: | 1.99 mmoles/g |
| degree of substitution cationic: | 0.59 |
| degree of substitution octyl: | 0.36 |

The measurement of the Staudinger index (eta) was carried out in an aqueous solution of 0.2 mole/liter of acetic acid and 0.1 mole/liter of sodium acetate (chitosan) and in an aqueous solution of 0.2 mole/liter of acetic acid and 0.1 mole/liter of sodium chloride (chitosan derivatives) at 25° C., using a DIN Ubbelohde capillary viscometer.

The determination of the degree of substitution was carried out as follows:

First the molar amount of titratable nitrogen ($N_t$) was determined by a non-aqueous titration with perchloric acid. The average molecular weight ($\overline{M}$) was computed therefrom as follows:

$$\overline{M}[g/mole] = \frac{1000}{N_t[mmole/g]}$$

Furthermore, $\overline{M} = 161 + (x \cdot 42) + (y \cdot 152) + (z \cdot m)$ molecular weight of a chitosan unit = 161 g/mole molecular weight of a quaternary group $R^2$ from the formula (I) ($R^4 = CH_3$; $X = Cl$) = 152 g/mole molecular weight of a —CO—CH$_2$— unit = 42 g/mole molecular weight of an alkyl group $R^3$ from formula (I) [$R^3$(octyl) = 129, $R^3$(tetradecyl) = 213, $R^3$(hexadecyl) = 241] = m, x = degree of substitution of the chitosan used (0.04 to 0.4), y = degree of substitution of cationic groups $R^2$, z = degree of substitution of alkyl groups $R^3$.

In order to compute the degree of substitution with the cationic groups $R^2$, the titratable quaternary nitrogen ($N_{tq}$) was first determined by a colloid titration with polyvinyl-potassium salt and the degree of substitution was then determined by means of the equation $$y = \frac{N_{tq} \cdot M}{1000}$$

The degree of substitution with alkyl groups was determined as follows:

$$z = \frac{M - 161 - (152 \cdot y) - (42 \cdot x)}{m}$$

EXAMPLE 5

Test to determine the surface-active properties of the chitosan derivatives of the Examples 1 to 4

A cationic chitosan derivative according to Example 2 to DE-OS No. 32 45 784 which contained glycidol as non-ionic component was used as comparison substance. The characteristic data of this compound are

| | | |
|---|---|---|
| Staudinger index (eta) | 65 | ml/g |
| titratable nitrogen | 3.07 | mmoles/g |
| degree of substitution cationic: | 0.22 | |
| degree of substitution glycidol: | 1.7 | |

(a) Foam-forming properties of a 0.5 percent aqueous solution (pH=5)

100 ml of a 0.5 percent aqueous solution of the chitosan derivative to be tested were shaken in a 250-ml measuring cylinder, closed with a ground glass stopper, by rotating the cylinder through 180 degrees ten times. The height of foam was then read (in ml). After 5 minutes the height of foam determined again.

| | Height of Foam [ml] | |
|---|---|---|
| Chitosan Compound Tested | immediately | after 5 minutes |
| according to Example 1 | 165 | 165 |
| according to Example 2 | 124 | 120 |
| according to Example 3 | 138 | 134 |
| accordng to DE-OS 32 45 784 | 103 | 100 |

95 g of a 0.5 percent aqueous-alcoholic solution (70:30) of the chitosan compound to be tested were drawn off together with 5 g of propane/butane (70:30) into a compressed gas package. Subsequently the foam volume of a sample weighing 10 g was determined.

The results of this test have been compiled in the Table hereafter

| Chitosan according to | Foam Volume [ml] | Foam Quality | Foam Stability |
|---|---|---|---|
| Example 1 | 150 | finely porous, primarily creamy | foam remains stable longer than 10 minutes |
| Example 2 | 100 | finely porous, primarily creamy | foam remains stable longer than 10 minutes |
| Example 3 | 120 | finely porous, primarily creamy | foam remains stable longer than 10 minutes |
| Example 4 | 110 | finely porous, primarily compact | foam remains stable longer than 10 minutes |
| DE-OS 32 45 784 | 15 | aqueous, no foam formation | unstable |

An attempt was made to produce an emulsion having the following composition:

| |
|---|
| 4 g of fatty alcohol |
| 1 g of chitosan derivative |
| 95 g of water |
| 100 g |

Result:
Chitosan Derivative according to Example 1 DE-OS No. 32 45 784 emulsion properties

| | |
|---|---|
| homogeneous | inhomogeneous |
| at 40° C. | not stable |
| stable on storage | on storage |

EXAMPLE 6

Foam Fixative

| | |
|---|---|
| 1.0 g | of quaternary, surface-active chitosan derivative according to Example 1 (eta = 74 ml/g; degree of substitution: cationic 0.42; octyl 0.31) |
| 30.0 g | of ethanol |
| 5.0 g | of propellant (propane/butane 70/30) |
| 0.2 g | of perfume oil |
| 63.8 g | of water |
| 100.0 g | |

An amount of the finely porous foam having approximately the size of a golf ball was spread over washed towel-dried hair.

As compared with a commercial foam fixative containing synthetic polymer the hair has a more pleasant and softer feel while the setting effect is good.

EXAMPLE 7

Hair Curative

| | |
|---|---|
| 1.0 | of quaternary, surface-active chitosan derivative according to Example 1 (eta = 74 ml/g; degree of substitution: cationic 0.42; octyl 0.31) |
| 4.0 g | of cetyl stearyl alcohol |
| 0.2 g | of perfume |
| 94.8 g | of water |
| 100.0 g | |

35 g of this curvative are distributed in the washed hair and are washed out again with water after a reaction time of 3 to 5 minutes.

As a result an excellent feel and sheen as well as a good combability of the hair were obtained.

EXAMPLE 8

Foam Permanent Wave

| | |
|---|---|
| 1.2 g | of quaternary surface-active chitosan derivative according to Example 2 (eta = 67 ml/g; degree of substitution: catatonic 0.53; hexadecyl 0.13) |
| 10.0 g | of thioglycolic acid |
| 8.0 g | of ammonia, 25 percent aqueous solution |
| 6.1 g | of ammonium hydrogen carbonate |
| 74.7 g | of water |
| 100.0 g | |

The active ingredient solution was drawn off with Propellant F 12/114 (1:1) in the ratio of 85:15.

For its application this aerosol foam was uniformly spread on the rolled-up, towel-dried hair and allowed to react for approximately 20 minutes. The hair was washed with water and oxidatively treated in a conventional manner.

A good wave result was obtained; the hair had a natural and soft feel.

EXAMPLE 9

Hair Fixative

| | |
|---|---|
| 1.3 g | of quaternary surface-active chitosan derivative according to Example 3 (eta = 97 ml/g; degree of substitution; cationic 0.51; tetradecyl 0.02) |
| 35.0 g | of isopropanol |
| 0.4 g | of formic acid, 10 percent aqueous solution |
| 0.2 g | of perfume oil |
| 63.1 g | of water |
| 100.0 g | |

20 ml of this solution were spread on the washed, towel-dried hair. The hair was then set and dried in a conventional manner.

As compared with a hair fixative based on chitosan-/formic acid the hair had a more pleasant and softer feel while the setting effect was good.

EXAMPLE 10

Shaving Foam 1.0 g of quaternary, surface-active chitosan derivative according to Example 1 (eta=74 ml/g; degree of substitution: cationic 0.42; octyl 0.31)

| | |
|---|---|
| 40.0 g | of ethanol |
| 0.5 g | of perfume |
| 0.2 g | of allantoin |
| 0.1 g | of preservative |
| 58.2 g | of water |
| 100.0 g | |

After shaving, the foam imparts a pleasant, smooth feeling to the skin and simultaneously it has a disinfecting effect.

EXAMPLE 11

Anionic Shampoo

| | |
|---|---|
| 1.0 g | of quaternary surface-active chitosan derivative according to Example 4 (eta = 406 ml/g; degree of substitution: cationic 0.59, octyl 0.36) |
| 40.0 g | of lauryl alcohol diglycol ether sulphate-sodium salt, 28 percent aqueous solution |
| 4.0 g | of sodium chloride |
| 0.10 g | of formaldehyde |
| 0.05 g | of dye |
| 54.85 g | of water |
| 100.00 g | |

A clear shampoo was obtained. The hair washed therewith was excellently conditioned with regard to feel, sheen and combability.

The outstanding foam properties of the shampoo due to the addition of the chitosan derivative must be particularly emphasized.

EXAMPLE 12

Hair Tonic in Foam Form

| | |
|---|---|
| 0.5 g | of quaternary, surface-active chitosan derivative according to Example 3 (eta = 97 ml/g; degree of substitution: cationic 0.51; tetradecyl 0.02) |
| 40.0 g | of ethanol |
| 0.3 g | of perfume oil |
| 59.2 g | of water |
| 100.0 g | |

After massaging the hair tonic into the scalp it imparts freshness and sheen to the hair.

EXAMPLE 13

Hair Curative

| | |
|---|---|
| 1.0 g | of quaternary surface-active chitosan derivative according to Example 1 (eta = 74 ml/g; degree of substitution; cationic 0.42; octyl 0.31) |
| 4.0 g | of coco (pentaethoxy) methyl ammonium chloride |
| 0.2 g | of perfume |
| 93.8 g | of water |
| 100.0 g | |

35 g of the above curative were spread in washed hair and washed out again with water after a reaction time of 3 to 5 minutes.

As a result an excellent feel and sheen as well as an outstanding combability were obtained.

EXAMPLE 14

Foam Fixative

| | |
|---|---|
| 1.0 g | of quaternary, surface-active chitosan, derivative according to Example 1 (eta = 74 ml/g; degree of substitution: cationic 0.42, octyl 0.31) |
| 30.0 g | of ethanol |
| 5.0 g | of propellant (propane/butane 70:30) |
| 2.0 g | of polyvinyl pyrrolidone-vinyl acetate copolymer (in the ratio 30:70) |
| 0.2 g | of perfume oil |
| 61.8 g | of water |
| 100.0 g | |

An amount of the finely porous foam having approximately the size of a golf ball was spread on washed and towel-dried hair, whereupon the hair was set in the usual manner.

The hair had a pleasant and soft feel while the setting effect was strong.

EXAMPLE 15

Roll-on Deo

| | |
|---|---|
| 1.0 g | of quaternary surface-active chitosan derivative according to Example 4 (eta = 406 ml/g; degree of substitution: cationic 0.59; octyl 0.36) |
| 40.0 g | of ethanol |
| 8.0 g | of basic aluminum chloride (aluminum hydroxy chloride) |
| 1.0 g | of perfume oil |
| 0.2 g | of allantoin |
| 0.1 g | of preservative |
| 49.7 g | of water |
| 100.0 g | |

All the data in percent relate to percent by weight.

While our invention has been illustrated and described as embodied in new surface-active, quaternary, N-substituted chitosan derivatives and cosmetic compositions based on them, it is not intended to be limited to the details shown, since various modifications and structural changes may be made without departing in any way from the spirit of our invention.

Without further analysis, the foregoing will so fully reveal the gist of our invention that others can, by applying current knowledge, readily adapt it for various applications without omitting features that, from the standpoint of prior art, fairly constitute essential characteristics of the generic or specific aspects of our invention.

What is claimed as new and desired to be protected by Letters Patent is set forth in the appended claims.

1. A cosmetic composition for the treatment of hair and skin which contains in a suitable cosmetic base a macromolecular, surface-active, quaternary N-substituted compound which is derived from chitosan and has the general formula (I)

$$HO[C_6H_{11-x-y-z}NO_4(R^1)_x(R^2)_y(R^3)_z]_pH \qquad (I),$$

wherein x can assume any numerical value from 0.04 to 0.4, y can assume any numerical value from 0.04 to 0.92 and z can assume any numerical value from 0.04 to 0.92 on the condition that $(x+y+z) \leq 2$, p represents an integer from 100 to 100,000, $R^1$ represents the radical $$-\underset{\underset{O}{\|}}{C}-CH_3,$$

$R^2$ represents the radical $$-CH\begin{matrix}CH_2OH\\ \\CH_2-N^\oplus(R^4)_3X^\ominus\end{matrix}$$

or $$+CH_2-\underset{\underset{CH_2-N^\oplus(R^4)_3X^\ominus}{|}}{CH}-O\!\!+\!\!_oH \quad,$$

wherein $R^4$ represents a to $C_4$-alkyl group, x represents Cl, Br, I or $CH_3SO_4$ and o represents an integer from 1 to 5, and $R^3$ represents the radical $$-\!\!+\!\!CH_2-\underset{\underset{(CH_2)_n-CH_3}{|}}{CH}-O\!\!+\!\!_oH,$$

wherein n represents an integer from 5 to 20 and o represents an integer from 1 to 5.

2. A macromolecular, surface-active quaternary N-substituted compound which is derived from chitosan and has the formula (I)

$$HO[C_6H_{11-x-y-z}NO_4(R^1)_x(R^2)_y(R^3)_z]_pH \qquad (I),$$

wherein x can assume any numerical value from 0.04 to 0.4, y can assume any numerical value from 0.04 to 0.92 and z can assume any numerical value from 0.04 to 0.92 on the condition that $x+y+z \leq 2$, p represents an integer from 100 to 100,000, $R^1$ represents the radical $$-\underset{\underset{O}{\|}}{C}-CH_3,$$

$R^2$ represents the radical $$-CH\begin{matrix}CH_2OH\\ \\CH_2-N^\oplus(R^4)_3X^\ominus\end{matrix}$$

or $$+CH_2-\underset{\underset{CH_2-N^\oplus(R^4)_3X^\ominus}{|}}{CH}-O\!\!+\!\!_oH \quad,$$

wherein $R^4$ represents a to $C_4$-alkyl group, X represents Cl, Br, I or $CH_3SO_4$ and o represents an integer from 1 to 5 and $R^3$ represents the radical $$-\!\!+\!\!CH_2-\underset{\underset{(CH_2)_n-CH_3}{|}}{CH}-O\!\!+\!\!_oH,$$

wherein n represents an integer from 5 to 20 and o represents an integer from 1 to 5.

3. A cosmetic composition according to claim 1, which contains 0.05 to 10.0% of said compound having said general formula.

4. A cosmetic composition according to claim 1 which is a solution.

5. A cosmetic composition according to claim 1 which is a cream.

6. A cosmetic composition according to claim 1 which is a gel.

7. A cosmetic composition according to claim 1 which is a dispersion.

8. A cosmetic composition according to claim 1 which is an emulsion.

9. A cosmetic composition according to claim 1 having a pH value of from 2 to 11.

10. A cosmetic composition according to claim 1, which contains a film-forming cosmetic polymer.

11. A cosmetic composition according to claim 1, which contains 0.01 to 2.0 percent by weight of at least one cosmetic dye which is a dye fixative.

12. A cosmetic composition according to claim 1, in which said cosmetic base comprises an aqueous preparation, which is mixed with a propellant liquifying under pressure and drawn off into a pressure vessel and is an aerosol foam.

13. A cosmetic composition according to claim 1, in which said cosmetic base comprises an aqueous-alcoholic preparation, which is mixed with a propellant liquifying under pressure and drawn off into a pressure vessel and is an aerosol foam.

14. A cosmetic composition according to claim 1 which comprises a shampoo containing at least one cationic, non-ionic, amphoteric or anionic surfactant.

15. A cosmetic composition according to claim 14, which contains 3 to 50 percent by weight of said surfactant and has a pH of between 3 and 9.

16. A composition according to claim 1, wherein o is from 2 to 5.

17. A compound according to claim 2, wherein o is from 2 to 5.

* * * * *